United States Patent [19]

Siddiqi et al.

[11] Patent Number: 4,960,693
[45] Date of Patent: Oct. 2, 1990

[54] SYSTEM OF REACTANTS INVOLVING AN APO-ENZYME USEFUL IN IMMUNOLOGICAL ANALYSIS AND A METHOD FOR CARRYING OUT IMMUOASSAYS WITH THIS SYSTEM

[75] Inventors: Iqbal Siddiqi, Geneva; Ciaron Mangan, Onex, both of Switzerland

[73] Assignee: Intracel Corporation, Bridgetown, Barbados

[21] Appl. No.: 151,279

[22] Filed: Jan. 6, 1988

[30] Foreign Application Priority Data

Jan. 6, 1987 [EP] European Pat. Off. ........ 87810005.6

[51] Int. Cl.$^5$ ................. G01N 33/535; G01N 33/542
[52] U.S. Cl. ........................................ 435/7; 435/15; 435/21; 435/24; 435/25; 436/501; 436/537
[58] Field of Search ................ 435/6, 7, 21, 810, 4, 435/15, 24, 25; 436/501, 537

[56] References Cited

U.S. PATENT DOCUMENTS

| | | | |
|---|---|---|---|
| 4,238,565 | 12/1980 | Hornby et al. | 435/7 |
| 4,473,638 | 9/1984 | Auditore-Hargreaves | 435/7 |
| 4,490,216 | 12/1984 | McConnell | 435/817 |
| 4,646,128 | 4/1987 | Chlebowski et al. | 435/7 |
| 4,666,830 | 5/1987 | Wagner | 435/7 |

FOREIGN PATENT DOCUMENTS

8808137 10/1988 Int'l Pat. Institute .
2267667 11/1987 Japan .
2023607 1/1980 United Kingdom .

OTHER PUBLICATIONS

E. E. Conn et al., *Outlines of Biochemistry*, 4th ed., John Wiley & Sons, Inc., New York, 1976, pp. 184–185.
B. L. Vallee et al., *Adv. Enzymol.*, 56, 341 ∝ 342, 1984.
Ngo et al, *Febs Letters*, 116, 285–288, 1980.
Morris, D. L., Ellis, P. B., Carrico, R. J., Yeager, F. M., Schroeder, H. R., Albarella, J. P. & Boguslaski, R. C., "Analytical Chemistry", vol. 53, No. 4, Apr. 4, 1981, pp. 658–665.
Schroeder, H. R., Johnson, P. K., Dean, C. L., Morris, D. L., Smith, D. & Refetoff, S., "Clinical Chemistry", vol. 32, Nov. 5, 1986, pp. 826–830.
Biological Abstracts, vol. 81, 1986, Abstract No. 81007001, Morikawa et al.

*Primary Examiner*—Esther L. Kepplinger
*Assistant Examiner*—David A. Saunders
*Attorney, Agent, or Firm*—Cushman, Darby & Cushman

[57] ABSTRACT

A quick and simple immunoassay technique applicable to the determination of large molecules like proteins, polynucleotides and others involves labelling competitive immunospecies with an enzyme as signal generator. This enzyme can be converted to the corresponding apo-enzyme form and its regeneration, upon addition of a suitable co-factor, is inhibited by complexation when the labelled specie is reacted with its immunopartner. The degree of complexation is therefore ascertained by measuring the extent of regenerated activity.

14 Claims, 1 Drawing Sheet

SYSTEM OF REACTANTS INVOLVING AN APO-ENZYME USEFUL IN IMMUNOLOGICAL ANALYSIS AND A METHOD FOR CARRYING OUT IMMUOASSAYS WITH THIS SYSTEM

INTRODUCTION

The present invention relates to immunoassay techniques and, more specifically, to a new system for generating detectable signals in enzyme labelled immunobinding reactions. The invention also relates to a method for using the new system and making it operational.

DESCRIPTION OF THE PRIOR ART

Measurement of substances in human and animal body fluids is of great importance in clinical chemistry and medicine. The increasing need for new assay methods which are quantitative, specific, and sensitive, has resulted in the development of competitive binding assays based on ligand-receptor, i.e. antigen-antibody interactions. Most enzyme immunoassay methods depend on competition of sample ligand and signal generating ligand e.g. enzyme labelled antigen, for a limited number of antibody (receptor) binding sites. The concentration of antibody sites available to bind the labelled ligand is inversely related to the concentration of unlabelled ligand analyte present in the sample.

However directly differentiating between the free and the immunobonded signal generator is not always possible and it is therefore necessary to physically or chemically separate labelled ligand bound to receptor from that which is unbound (Heterogeneous immunoassay). This operation is time consuming, inconvenient, and can contribute significantly to the error of the measurement. Extensive description of heterogeneous type enzyme immunoassays exist already in the litterature; the most useful are to be found in Edward T. Maggio Enzyme-Immunoassay, CRC press, Inc. 1981. Also of interest are publications by Van Weemen et al, FEBS Letters 14, 232 (1971), and Engvall et al, Immunochemistry, 8, 871 (1971) concerned with immunoassays employing enzymes. See also U.S. Pat. No 3,654,090.

Homogeneous enzyme immunoassay is one technique that avoids the problem of separation. Homogeneous enzyme immunoassays usually depend upon a change in the specific marker activity when antibody is bound to the labelled antigen. For instance, assuming that the marker is an enzyme, the change is related to bound enzyme reactivity toward some enzyme substrate. Thus, the activity of the unseparated assay mixture responds to the proportion of enzyme labelled antigen to which antibody is bound; hence no separation step is required. The technique has been successfully applied to the measurement of small haptenic molecules such as drugs. This is commonly known as the Enzyme Multiplied Immunoassay Technique and systems of this kind have been commercialized under the trade name EMIT; Syva, Maidenhead, U.K.); it was first described by Rubenstein et al. Biochem Biophys Res Commun 47 846 (1972) see also U.S. Pat. No 3,817,837 and 4,233,401.

Four distinct variants of the homoqeneous enzyme immunoassay principle have been devised and developped commercially.

(1) The earliest EMIT systems employ lysozyme as the enzyme label and this technique is still used today in assays for drugs of abuse. Here the effect is one of inhibition of the activity of enzyme-hapten conjugates as a result of antibody binding. This system has also been demonstrated with enzymes requiring smaller substrates, such as malate dehydrogenase and glucose-6-phosphate dehydrogenase for the assay of therapeutic drugs as described by Rowly et al, J. Biol. Chem. 250, 3739 (1975). See also U.S. Pat. No 4,233,401 and Clin. Chem. 22, 1185 (1976).

(2) Another type of assay involves the stimulation or restoration of activity of an inhibited enzyme-hapten conjugate when an antibody binds to it as demonstrated by the thyroxine-malate dehydrogenase conjugate. In this case, enzyme activity is substantially inhibited upon formation of the conjugate. However, enzyme inhibition is reversed when the conjugate binds to the antibody. This is described by Ullman et al, Biochim. Biophys. Acta. 66, 567 (1979).

(3) There is also a homogeneous immunoassay for haptens using a prosthetic group (FAD) as a label joined to the ligand analyte which may combine, as a co-factor, with an appropriate apoenzyme to regenerate a corresponding holoenzyme system allowing detection.

Immunoassays are performed without separation of antibody-bound label from free label since the ability of the prosthetic group residue to regenerate active holoenzyme is substantially inhibited when labelled ligand is complexed to its antibody. Thus, to make the system operative, the specific binding reaction is initiated, excess apoenzyme is added and the resulting holoenzyme activity is related to the amount of unlabelled ligand in the solution. This system is described by Morris et al., Anal. Chem. 53, 658 (1981.)

(4) The previous three systems describe assays for small molecules but since 1979 homogeneous immonoassay have been applied to the measurement of proteins. Here instead of using the conformational effects of the binding of the antibody to the enzyme-labelled antigen, steric exclusion of a macromolecular substrate by antibody binding is used. The enzyme beta galactosidase (the marker) is conjugated to the protein analyte, antibody binds thereto and excludes access of the marker to the substrate onitrophenyl galactoside which has been converted to macromolecular form by attachment to a dextran carrier via a hydrophobic spacer. Inhibition of enzyme of up to 80% was observed as a result of excess binding of the antibody providing the basis for the homogeneous assay of free antigen. This technique is described by Gibbons et al, Clin. Chem., 27, 1602 (1979). Other variants of homogeneous immunoassays that have been disclosed but which are inherently more complicated and thus expensive in design and operation are:

(1) Enzyme enhancement immunoassay. Here the antibody is labelled and the system depends upon the formation of an insoluble enzyme product from the immune complex which can be detected by light scattering. The product formed by the free enzyme is soluble, thus the amount of antigen in the test modulates the degree of light scattering. This is described by Gibbons et al. Clin. Chem. 27 1602. (1981)., and U.S. Pat. No 4,281,061.

(2) Enzyme channelling immunoassay. The immune reaction here places two enzymes that catalyse consecutive reactions in close proximity resulting in an accelerated conversion of product. The reaction is monitored by NADH production. Litman et al, Anal. Biochem., 106.223. (1980). See also U.S. Pat. No 4,238,565.

Although the above-reviewed techniques have merit and are being successfully used in many fields of bioanalysis, there is still a need for immunoassay systems and methods offering enhanced selectivity in the analysis of complex media, enhanced sensitivity to increase detection thresholds and improved simplicity for being extensively used in kit form by unspecialized operators.

SUMMARY OF THE INVENTION

The system of reactants, as summarized in claim 1, is one further step toward the desired objectives. Briefly, we deal here with a new type of homogeneous enzyme immunoassay using an apoenzyme which, as stated before, is an enzyme that has had its co-factor removed and is thus inactive. Normally, we have an equilibrium: holoenzyme⇌apoenzyme + cofactor. The cofactor can be a metal ion which is bound to the protein by electrostatic forces, $\pi$ bonding; or charge transfer. The exact nature of binding is not clear. If the metal ion (which can be zinc, magnesium cadmium or transition metals) is removed with a sequestrant, the enzyme becomes deactivated but, normally, the activity is restored by the addition of a metal ion. The present assay advantageously exploits the differences in the reactivation kinetics of an apoenzyme-ligand conjugate when it is (a) free in solution, and (b) bound to a receptor, e.g. an antibody. It has been found that the binding of an antibody to an apoenzyme-ligand conjugate in an immune reaction influences the rate of re-activation of the apoenzyme in the complex to form a fully functioning holoenzyme. A dose response curve for the ligand (antigen) indicated that the assay can be used in an homogeneous enzyme immunoassay format. It should be clear that, in this invention, the definitions of a ligand (antigen) (and its receptor antibody) are relative since an antibody (receptor) to an antigen (ligand)can also be a ligand (antigen) to another receptor (antibody). Consequently, the words antibody and antigen can interchangeably be used for the ligand to receptor partners of a binding pair. The enzyme to be used in the system can be calf intestine alkaline phosphatase although, naturally, other enzymatic systems with comparable properties are also possible. This is a non-specific enzyme capable of hydrolysing compounds containing phosphomonoesters and pyrophosphates. Alkaline phosphatase is a zinc dependent metalloenzyme that also has slight dependence on cobalt and lead ions. Enzyme activity is dependent upon the presence of zinc as co-factor at the active site of the enzyme molecule. The zinc can be quite easily complexed out of the enzyme by a chelating agent, e.g. ortho-phenanthroline (OP), 8-aminoqinoline and $\alpha$, $\alpha'$-dipyridyl; the removal of the zinc cations results in complete deactivation, i.e. conversion into the apoenzyme form. Complete and instantaneous reactivation can be demonstrated by adding zinc back into the apoenzyme solution. Other metals such as Co, Mn, Pb, Cu, Ni, Fe can also restore enzyme activity (see D. J. PLOCKE et al., Biochemistry 1 (1962), 1039–1041). Other chelating agents such as $\alpha,\alpha'$-dipyridyl, 8-aminoquinoline and other sequestrants disclosed in B. L. VALEE et al., Advances in Enzymology 56, (1984), page 301. Chelatants such as ethylene diamine tetracetic acid EDTA) or nitrilotriacetic acid (NTA) which have complexing affinity for protein structures should be avoided in this cases, although they can be used with other enzymes, particularly with enzymes having high binding affinity for metals, e.g. oxidases. When the apoform of alkaline phosphatase is bound to a protein ligand, for instance IgG, a labelled reagent capable to compete with free IgG in an immuno-reaction is produced. Reactivation of this apoenzyme conjugate can be effected unless involved in an immunochemical reaction. By immunochemical reaction it is meant that there is a reaction between the two partners of an immunopair, e.g. an antigen or antibody from antiserum raised against the immunoglobulin of the conjugate.

REFERENCES UNCOVERED BY THE EUROPEAN SEARCH REPORT

Document (1), GB-A-2,023,607 (MILES) discloses using a prosthetic co-factor labelled ligand as a competitive immunoreagent in an immunoreaction for the determination of said ligand in an analyte. In contrast, in the method of the present invention, immunoassays are performed using an apo-enzyme labelled immunoreagent to compete with an unlabelled analyte. Then a cofactor is added to regenerate the activity (in holoform) of the unused labelled reagent which can be then ascertained by its action on an appropriate substrate. Document (1) thus does not disclose an apoenzyme label and is therefore different from the present invention.

Document (2), Analytical Chemistry 53, No 4, April 1981, 658–665, discloses the use of a prosthetic flavine-adeninedinucleotide (FAD) group of apoglcose oxidase as a label for a ligand in competitive immunoreactions. The scheme is therefore the same as in document (1); document (2) is therefore neither anticipating.

Document (3), US-A-4,473,638 (DU PONT) also involves an FAD-ligand conjugate.

Document (4), US-A-4,238,,565 (MILES LABORATORIES) appears to be the patent version of document (2).

Document (5), Biological Abstracts 82 (1986), 82 033 303 discloses the immunodetermination of thyroxin-binding globulin (TBG) with NG-aminohexyl-FAD labelled TBG. The scheme is still like in the previous document.

DETAILED DESCRIPTION OF THE INVENTION

The various experiments, the results of which provided the present invention were carried out in the following manner.

1. The kinetics of deactivation and reactivation of alkaline phosphatase in the presence of zinc sequestrants were investigated.

2. Deactivation and reactivation kinetics for the enzyme when conjugated to an immunoglobulin molecule were also studied and found to be quite comparable to that of the free enzyme.

3. Deactivation and reactivation kinetics for the conjugate when involved in immunochemical reactions was also studied. Reactivation was found to be nearly completely blocked after coupling the ligand to specific antisera.

Details on these experiments are given below for which reference is made to the annexed drawings.

More specifically, alkaline phosphatase solutions were incubated overnight with solutions of 0-phenantroline (the chelating agent) of various concentrations in order to determine the required amount of chelatant to bring about enzyme deactivation (i.e. to convert to apoenzyme form). In short, when starting with a $10^{-10}$ molar solution of the enzyme, significant deactivation occurs after adding one aliquot of a $10^{-5}$ molar solution of 0-phenantroline. Complete deactivation occurs when using a same amount of a $10^{-3}$ solution (cf. FIG. 1 curve A)

Figure 1:
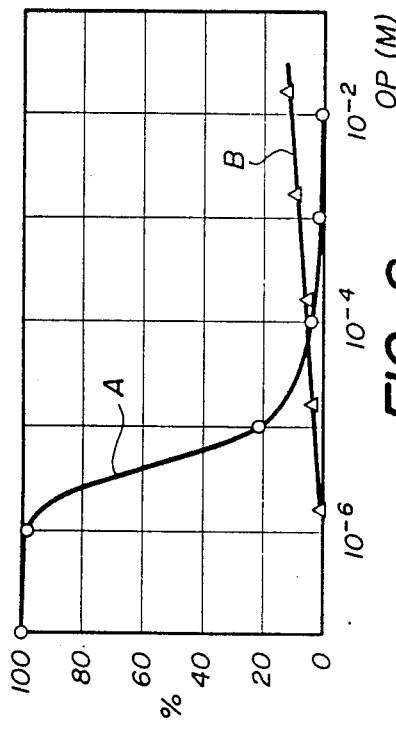
FIG. 1 is a diagram showing the variation of enzymic activity toward p-nitrophenyl phosphate of alkaline phosphatase upon deactivation by progressively increasing quantities of a zinc chelating agent, o-phenantroline (A) and reactivation with zinc cations (B).

Reactivation of the apoenzyme was carried out by adding increasing Zn (in the form of sulfate or chloride) to a solution of the enzyme ($10^{-10}$ molar) deactivated beforehand with an aliquot of $10^{-2}$ molar 0-phenantroline. FIG. 1, curve B shows that a $3 \times 10^{-4}$M solution of zinc ions is sufficient to restore about 70–80% of the initial rate activity. Further concentration of zinc will progressively bring the activity to its original level (100%).

Figure 2:
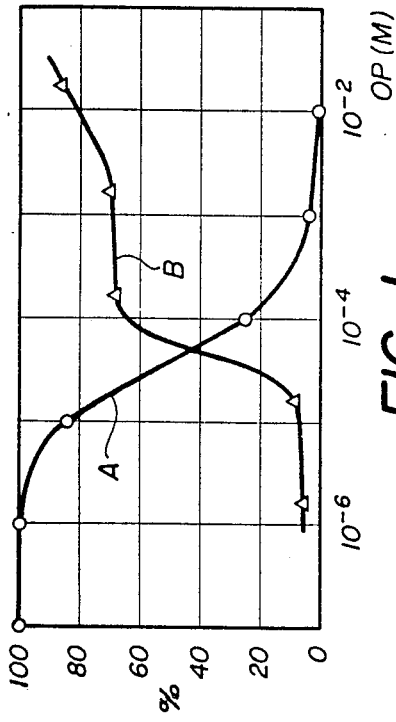
FIG. 2 is a diagram similar to that of FIG. 1, but concerning an alkaline phosphatase-labelled protein, i.e. an immunoglobulin-enzyme conjugate.

In order to compare the results of the foregoing experiments with that from a ligand labelled with alkaline phosphatase, a conjugate with rabbit anti-human IgG antibody was used (the rabbit antibody to human IgG is considered the ligand in this case). FIG. 2, curve A shows that the effect of a $10^{-5}$ molar solution of the 0-phenanthroline (O.P.) is significant whereas a $10^{-3}$ to $10^{-2}$ M solution totally inhibits the enzymatic activity of the apoenzyme/ligand conjugate. Addition of zinc to the inhibited conjugate only partially restores the original activity (see FIG. 2, curve B); however the reactivation level of the conjugate is sufficient for it being subsequently used as a labelled reagent in analytical immunoreactions.

Figure 3:
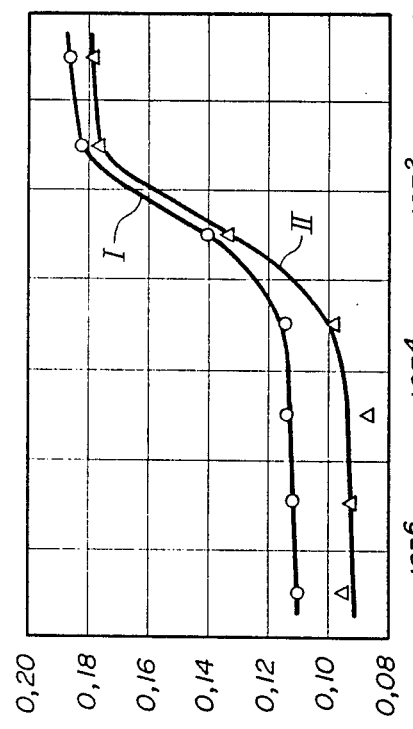
FIG. 3 is a diagram showing the variation of the activity recovery with Zn of an apo-alkalinephosphatase/ligand conjugate as a function of the extent of immuno-complexation with an antibody specific to that ligand.

Thus, the apo-alkaline phosphatase/rabbit IgG conjugate (Ag*) was coupled to an antibody (Ab), i.e. an antiserum against rabbit IgG raised in a donkey. After inhibitions with the chelating agent ($10^{-2}$M O.P.) excess zinc ($3 \times 10^{-3}$M) was added for activity restoration. FIG. 3 shows that restoration increases with decreasing amounts of antibody binding to the conjugate. In this figure, 100% corresponds to total maximum recovery, the conjugate in the absence of the antibody being taken as the reference level (see FIG. 2, curve B).

Figure 4:
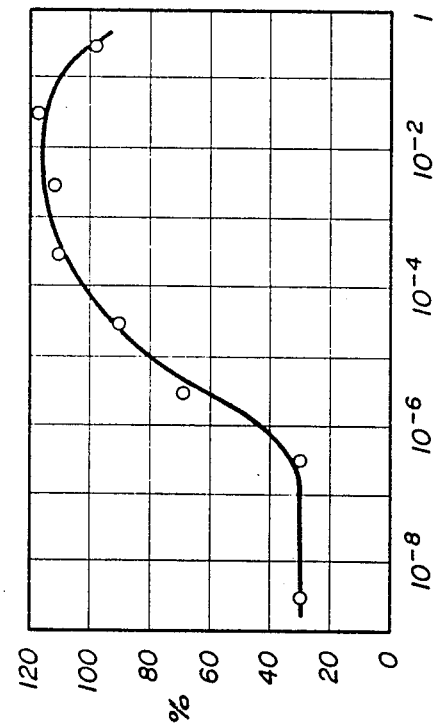
FIG. 4 is a diagram illustrating a competitive immunoassay between an unlabelled ligand (an analyte Ag) and a ligand labelled with alkaline apo-phosphatase (Ag*) in a test involving the restoration of enzyme activity with zinc after deactivation with ortho-phenanthroline.

FIG. 4 illustrates a typical case of competitive immunoassay between rabbit IgG and rabbit IgG labelled with the apoform of alkaline phosphatase (Ag*) toward donkey antiserum Ab). The concentration of Ag* was kept constant ($2,3 \times 10^{-7}$M), the concentration of the chelating agent (O.P.). was $10^{-2}$M, that of restoring $Zn^{++}$, $3 \times 10^{-'}$ and the amount of unlabelled antigen was varied from $2 \times 10^{-7}$ to $2 \times 10^{-1}$M. In FIG. 4, curve I refers to the situation when blocking of the conjugate was effected with a quantity of Ab corresponding to $4 \times 10^{-3}$M; curve II refers to when Ab was $4 \times 10^{-4}$M.

Other holoenzyme/apoenzyme systems are also usable in the present invention. A non exhaustive list of such enzymes is given below:

Some oxidoreductases, e.g. Superoxide dismutase incorporating $Cu^{++}$ and $Zn^{++}$ ions in 1:1:1 mole ratio in the active site and galactose oxidase incorporating $Cu^{++}$ in a 1:1 mole ratio.

A transferase, e.g. aspartate transcarbamylase which binds $Zn^{++}$ in a 6:1 mole ratio.

Hydrolases: Alkaline phosphatase incorporating mainly $Zn^{++}$ in a 4:1 mole ratio. Leucine aminopeptidase with $Zn^{++}$ in a 2:1 mole ratio. If $Co^{++}$ is incorporated instead of zinc ions, the restored enzyme is 15 times more active. Thermolysin takes up $Zn^{++}$ ions in a 1:1 mole ratio and $Cu^{++}$ ions in a 4:1 mole ratio.

Lyases: Aldolase incorporates 1 mole of $Zn^{++}$/mole of enzyme; carbonic anhydrase also incorporates 1 mole of zinc/mole of enzyme; $Co^{++}$ can be taken instead of zinc (see Advances in Enzymology 56 (1984), 283).

EXPERIMENTAL SECTION

EXAMPLE 1

Alkaline phosphatase deactivation and reactivation

Enzyme assay: the measurement system in all cases involved the addition of 50 μl of enzyme or enzyme/ligand conjugate solution (at a given concentration) to 1450 μl of enzyme substrate, i.e. 1 mMolar PNPP (p-nitrophenol phosphate) in 1Molar Tris/HCl pH 8.0. is an analytical cuvette. The enzyme catalyzes the hydrolysis of p-nitrophenyl phosphate (the substrate) to P nitrophenol, a yellow product, which is analyzed colorimetrically according to usual means. Rates of reaction at 405 nm were read over a five minute period. In the case of zinc reactivation, 50 μl of stated zinc concentration (see later) were added after one minute to the 1500 μl reaction volume to cause reactivation and the corresponding rate was then measured.

A $10^{-10}$M concentration of stock enzyme in PNPP (enzyme substrate) solution was used as the standard rate of native enzyme activity. Enzyme at this concentration was incubated overnight in the presence of a chelatant, i.e. a range of 0-phenantroline (O.P.) concentrations from $10^{-2}$M to $10^{-6}$M. The chelating agent totally inhibited enzyme activity at a concentration of $10^{-2}$ Molar as seen in FIG. 1, curve A:

To measure reactivation, apoenzyme in the presence of $10^{-2}$M of O.P. was added to the substrate solution. After one minute zinc concentrations from $3 \times 10^{-6}$M to $3 \times 10^{-2}$M were added to a series of cuvettes containing the reaction volume and the immediate effects upon the reaction velocity were measured. It was found that activity which is completely abolished by incubation in $10^{-3}$M of O.P. is restored instantaneously and almost completely on addition of $3 \times 10^{-3}$M $Zn^{++}$ as shown in FIG. 1, curve B.

EXAMPLE 2

Deactivation and reactivation of alkaline phosphatase when conjugated to a ligand The same experiments were carried out to obtain the kinetic data for inhibition and re-activation when the enzyme was conjugated to a ligand molecule. In this case alkaline phosphatase conjugated to rabbit anti-human IgG antibody was used. The product was bought from DAKO, Denmark It was found that 1/150 dilution of the stock conjugate (2,3 $10^{-7}$M) gave a similar rate response to that of the native enzyme dilution used above. Again a $10^{-2}$M concentration of O.P. was found to totally inhibit the activity of the enzyme even when conjugated to IgG as seen in FIG. 2, curve A.

Recovery of activity of the enzyme conjugate up to the level of the non-deactivated conjugate was not observed upon addition of zinc to the reaction mixture. Maximum activity at $3\times10^{-2}$M zinc added to the apoenzyme conjugate solution in the presence of $4\times10^{-3}$M O.P. was only 10–20% that of the normal value of the conjugate as seen in FIG. 2, curve B. This gave an indication that conjugating the enzyme to a similar sized protein (molecular weight of IgG =150,000, Molecular weight of calf intestine alkaline phosphatase =140,000) was altering the kinetics of its re-activation with zinc compared to reactivation kinetics of the lone apoenzyme.

Nevertheless reactivation, as compared to that of the corresponding immunocomplex (see hereafter) was sufficient for using the present apo-enzyme conjugate as a competitive labelled reagent (Ag*) in subsequent immunotests.

Thus, the above apo-alkaline phosphatase/rabbit anti-human IgG conjugate was immunocomplexed with antiserum against rabbit IgG raised in a donkey (dilutions of stock solution, ($10^{-7}$M) $1/10^8$ to $\frac{1}{2}$). Serial dilutions of the donkey antirabbit antiserum were incubated with the apoenzyme/rabbit IgG conjugate in the presence as before of $10^{=2}$M O.P. Zinc was added afterwards at a concentration of $3\times10^{-3}$M and the restored activity was measured. The results are summarized in FIG. 3 which shows that the more antibody in the assay medium toward the apoenzyme-ligand conjugate, the less the enzyme activity is rescued. In this situation, there is a high probability that any specific immunological binding by the antiserum will be towards the Fc. region of the IgG molecule where the enzyme molecule is most likely to be conjugated. The donkey anti-serum is very high in total protein content and, as shown, there is a decrease in the level of reactivation by added zinc from the regions of high antiserum concentration. It is of interest to note that at low concentrations of the antiserum, reactivation is 20% that of the standard non-deactivated conjugate value.

It was noted that at saturating levels of antiserum there is a decrease of enzyme reactivity and a corresponding increase in reactivity at lower levels of specific binding to the conjugate. It was thought that this effect may be due to the high levels of protein content present in the reaction mixture. High levels of non-specific protein were thus added to the apoenzyme conjugate after inactivation by O.P. and again recovery of activity by zinc addition was measured. The four proteins tested, Human serum albumin (a), Bovine serum albumin (b), Rabbit anti-serum (c) and non-specific donkey anti-serum (d), had no effect on the recovery of the apoenzyme activity with addition of zinc as all values returned to the level found for the normal value of reactivity of the apoenzyme conjugate without antibody against the conjugate as shown in the Table below. This test is evidence that any effects observed are specific for the binding of antibody in the region of the apoenzyme conjugated to the IgG molecule. In the table below activities are referred to the native conjugate taken as 100%.

|  | Apoconjugate with O.P. present (dil. 1/150) | plus (a) (500 μg/l) | plus (b) (500 μg/l) | plus (c) (500 μg/l) | plus (d) (500 μg/l) |
| --- | --- | --- | --- | --- | --- |
| Activity (no Zn) | 0 | 0 | 0 | 0 | 0 |
| Activity % (with Zn, $10^{-3}$M) | 62,5 | 65 | 64 | 63 | 66 |

EXAMPLE 3

Competitive test

A dose response experiment for the non labelled antigen analyte was carried out. This is a simple type of immunoassay format where the apoenzyme form of alkaline phosphatase labelled antigen, rabbit IgG, is displaced from the complex by increasing the concentration of competing non-labelled rabbit IgG, which is present in the form of a serial dilutions of rabbit antiserum. Serial dilutions of the unlabelled antigen ($2\times10^{-7}$ to $2\times10^{-1}$M), rabbit IgG, were incubated first with the antibody ($4\times10^{-3}$M or $4\times10^{-4}$M) for thirty minutes. The labelled antigen (apoenzyme conjugated to rabbit IgG, $2\times 10^{-1}$M) was then added and incubation proceeded for two hours. The final concentrations of the three reactants are as shown in FIG. 4. Thus the two fixed antibody concentrations were tested in the presence of serial dilutions of the unlabelled antigen and a fixed concentration of the labelled antigen. The labelled antigen concentration was kept constant throughout. FIG. 4 shows a sigmoidal dose response curve for the assay of rabbit IgG In both cases about 50% of the maximum available signal is modulated over the range of rabbit IgG concentrations from 0.7 nM to 70 nM.

We claim:

1. An assay for a bioreactive ligand species, comprising:
   providing a labelled ligand species, wherein said labelled ligand species is a conjugate of said bioreactive species and an apoenzyme;
   contacting a sample possibly containing said bioreactive ligand species with a known amount of a receptor which is specific for said bioreactive ligand species to produce a ligand-receptor species;
   contacting said ligand-receptor species with a solution of said labelled ligand species to produce a mixture comprising a labelled ligand-receptor species and said ligand-receptor species;
   contacting said mixture with an excess of a metal ion cofactor capable of converting said apoenzyme to the corresponding holoenzyme; and
   determining the conversion of said apoenzyme to said holoenzyme as a measure of said bioreactive species.

2. The assay defined in claim 1, wherein said conjugate is obtained by conjugating said bioreactive ligand species with a holoenzyme containing said metal ion cofactor and subsequently removing said metal ion cofactor.

3. The assay defined in claim 2, wherein said cofactor is removed by contacting said holoenzyme with a chelating agent.

4. The assay defined in claim 3, wherein said chelating agent is selected from the group consisting of o-phenanthroline, 8-aminoquinoline and $\alpha,\alpha'$-dipyridyl.

5. The assay defined in claim 4, wherein the apoenzyme is apoalkaline phosphatase and the cofactor is $Zn^{+2}$.

6. The assay defined in claim 5, wherein the bioreactive ligand species is an immunoglobulin.

7. The assay defined in claim 6, wherein said immunoglobulin is IgG originating from a human, rabbit or donkey.

8. The assay defined in claim 1, wherein said conjugate contains a covalently linked bridge of sufficient length to insulate the apoenzyme from stearic inhibition by said bioreactive species.

9. The assay defined in claim 1, wherein said apoenzyme is derived from superoxide dismutase and said cofactor is both $Cu^{2}+$ and $Zn^{2}+$.

10. The assay defined in claim 1, wherein said apoenzyme is derived from galactose oxidase and said cofactor is $Cu^{2}+$.

11. The assay defined in claim 1, wherein said apoenzyme is derived from aspartate transcarbamylase and said cofactor is $Zn^{2}+$.

12. The assay defined in claim 1, wherein said apoenzyme is derived from leucine aminopeptidase and said cofactor is selected from the group consisting of $Zn^{2}+$ and $Co^{2}+$.

13. The assay defined in claim 1, wherein said apoenzyme is derived from aldolase and said cofactor is $Zn^{2}+$.

14. The assay defined in claim 1, wherein said apoenzyme is derived from carbonic anhydrase and said cofactor is selected from the group consisting of $Zn^{2}+$ and $Co^{2}+$.

* * * * *